(12) United States Patent
Periard Larrivee et al.

(10) Patent No.: US 12,392,705 B2
(45) Date of Patent: Aug. 19, 2025

(54) DEVICE FOR THE DIRECT MEASUREMENT OF POROUS MEDIUM PARAMETERS

(71) Applicant: HORTAU INC., Levis (CA)

(72) Inventors: Yann Periard Larrivee, Saint-Luc-de-Bellechasse (CA); Vincent Pelletier, Sainte-Henedine (CA)

(73) Assignee: HORTAU INC., Levis (CA)

( * ) Notice: Subject to any disclaimer, the term of this patent is extended or adjusted under 35 U.S.C. 154(b) by 533 days.

(21) Appl. No.: 17/762,595

(22) PCT Filed: Sep. 25, 2020

(86) PCT No.: PCT/CA2020/051282
§ 371 (c)(1),
(2) Date: Mar. 22, 2022

(87) PCT Pub. No.: WO2021/056113
PCT Pub. Date: Apr. 1, 2021

(65) Prior Publication Data
US 2022/0397509 A1    Dec. 15, 2022

Related U.S. Application Data

(60) Provisional application No. 62/906,850, filed on Sep. 27, 2019.

(51) Int. Cl.
*G01N 15/08* (2006.01)
*G01N 33/24* (2006.01)

(52) U.S. Cl.
CPC ......... *G01N 15/082* (2013.01); *G01N 33/245* (2024.05); *G01N 33/246* (2013.01)

(58) Field of Classification Search
CPC .... G01N 33/24; G01N 33/245; G01N 33/246; G01N 15/08; G01N 15/082; G01N 13/00; G01N 13/04
See application file for complete search history.

(56) References Cited

U.S. PATENT DOCUMENTS 4,137,931 A * 2/1979 Hasenbeck .......... A01G 25/167
324/696
4,220,152 A * 9/1980 Dresback ............. A61K 9/0068
604/500

(Continued)

FOREIGN PATENT DOCUMENTS

CN    103884830 A  *  6/2014
WO    2020077440 A1   4/2020

OTHER PUBLICATIONS

Machine translation of CN 103884830 A (Year: 2014).*

(Continued)

*Primary Examiner* — Nathaniel J Kolb
(74) *Attorney, Agent, or Firm* — BCF LLP

(57) ABSTRACT

The present technology generally relates to a porous medium parameter measurement device comprising one or more component selected from: a porous conductive component; a porous non-conductive component; and a selective component. The one or more component is in operative communication with each one of the one or more component and with a porous medium through a plurality of pores allowing a porous medium solution to reach diffusion equilibrium between the porous medium and each of the one or more component. The one or more component allows direct measurement of a multiplicity of parameters of the porous medium solution.

14 Claims, 3 Drawing Sheets

(56) References Cited

U.S. PATENT DOCUMENTS

| | | | |
|---|---|---|---|
| 5,179,347 A * | 1/1993 | Hawkins | G01N 27/121 |
| | | | 324/696 |
| 7,927,883 B2 | 4/2011 | Tuli et al. | |
| 2009/0166520 A1* | 7/2009 | Tuli | G01V 9/00 |
| | | | 250/281 |
| 2010/0194411 A1* | 8/2010 | Caron | G01N 27/048 |
| | | | 324/694 |
| 2010/0263436 A1 | 10/2010 | Caron et al. | |
| 2014/0125360 A1* | 5/2014 | Goodchild | G01N 27/223 |
| | | | 29/729 |
| 2017/0307452 A1* | 10/2017 | Lafian | G01N 7/10 |

OTHER PUBLICATIONS

International Search Report of International Application No. PCT/CA2020/051282; Search Issued on Nov. 23, 2020; Authorized Officer: Samin Imam.

\* cited by examiner

DEVICE FOR THE DIRECT MEASUREMENT OF POROUS MEDIUM PARAMETERS

CROSS-REFERENCE TO RELATED APPLICATIONS

This application is a national phase filing under 35 U.S.C. 371 of International Application No. PCT/CA2020/051282 filed on Sep. 25, 2020, which claims the benefit of U.S. Provisional Application No. 62/906,850, filed on Sep. 27, 2019, the disclosure of both of which is incorporated herein by reference in its entirety.

TECHNICAL FIELD

The present technology generally relates to devices for the direct and/or simultaneous assessment and/or measurement of a multiplicity of parameters of a porous medium solution as well as to methods of using such devices.

BACKGROUND INFORMATION

Water conservation is becoming increasingly important. As global temperatures reach record highs, severe drought limits the water supply to farms, cities, industries, and ecosystems. Over-irrigation can contribute to water shortages and suppress biodiversity by leaching nutrients that cause eutrophication. Improving irrigation accuracy could provide significant environmental and economic benefits worldwide.

One way to conduct irrigation is to schedule it based on the monitoring, management, and data of soil water tension (SWT). With the invention of tensiometers, SWT measurements have been used to determine optimal scheduled irrigation times. Precise irrigation scheduling based on SWT criteria is a powerful method to optimize plant performance. By adjusting the amount and duration of irrigation to achieve an ideal SWT, it is possible to simultaneously achieve high productivity and meet environmental stewardship goals for water use and reduced leaching nutrients that cause eutrophication of watercourse. Other parameters may need to be monitored as well, such as soil solute content and or soil salinity. For soils with high salt content or for irrigated lands needing a large amount of fertilizers, salt build up in the root zone can have detrimental effects on plants growth. Such may be alleviated by leaching excess salts into the environment through abundant irrigation. Regular monitoring of soil salinity linked to electrical conductivity is required to avoid any detrimental impact on the environment.

Being able to precisely and accurately measure parameters of a porous medium such as, for example, soil, is of critical importance to derive irrigation schedule of cultures. What is needed is a field instrument that can measure soil parameters such as for example, soil salinity, directly and in real time without having to rely on data derived from empirical equations such as in conventional soil moisture or salinity probes.

It is thus an object of the present technology to provide porous medium parameter measurement device that alleviate at least some of these problems and that allow to provide more accurate measurements of various parameters of a porous medium.

SUMMARY OF THE DISCLOSURE

In various aspects, the present technology relates to a porous medium parameter measurement device comprising one or more component selected from: a porous conductive component; a porous non-conductive component; and a selective component; wherein each of the one or more component is in operative communication with each other and with a porous medium through a plurality of pores allowing a porous medium solution to reach diffusion equilibrium between the porous medium and each of the one or more component; and wherein the one or more component allows direct measurement of a multiplicity of parameters of the porous medium solution.

In various aspects, the present technology relates to a porous medium parameter measurement device comprising a multiplicity of components selected from at least two of the following components: a porous conductive component; a porous non-conductive component; and a selective component. In some implementations, the components may be present more than once in the porous medium parameter measurement device and wherein the components are in operative communication with one another and with a porous medium through a plurality of pores allowing a porous medium solution to reach diffusion equilibrium between the porous medium and each of the multiplicity of components thereby allowing the simultaneous measurement of a multiplicity of parameters.

Other aspects and features of the present disclosure will become apparent to those ordinarily skilled in the art upon review of the following description of specific embodiments.

BRIEF DESCRIPTION OF THE DRAWINGS

Further aspects and advantages of the present technology will become better understood with reference to the description in association with the following in which.

The various embodiments of the present technology will hereinafter be described in conjunction with the appended drawings, wherein like designations denote like elements.

DETAILED DESCRIPTION

Figure 1:
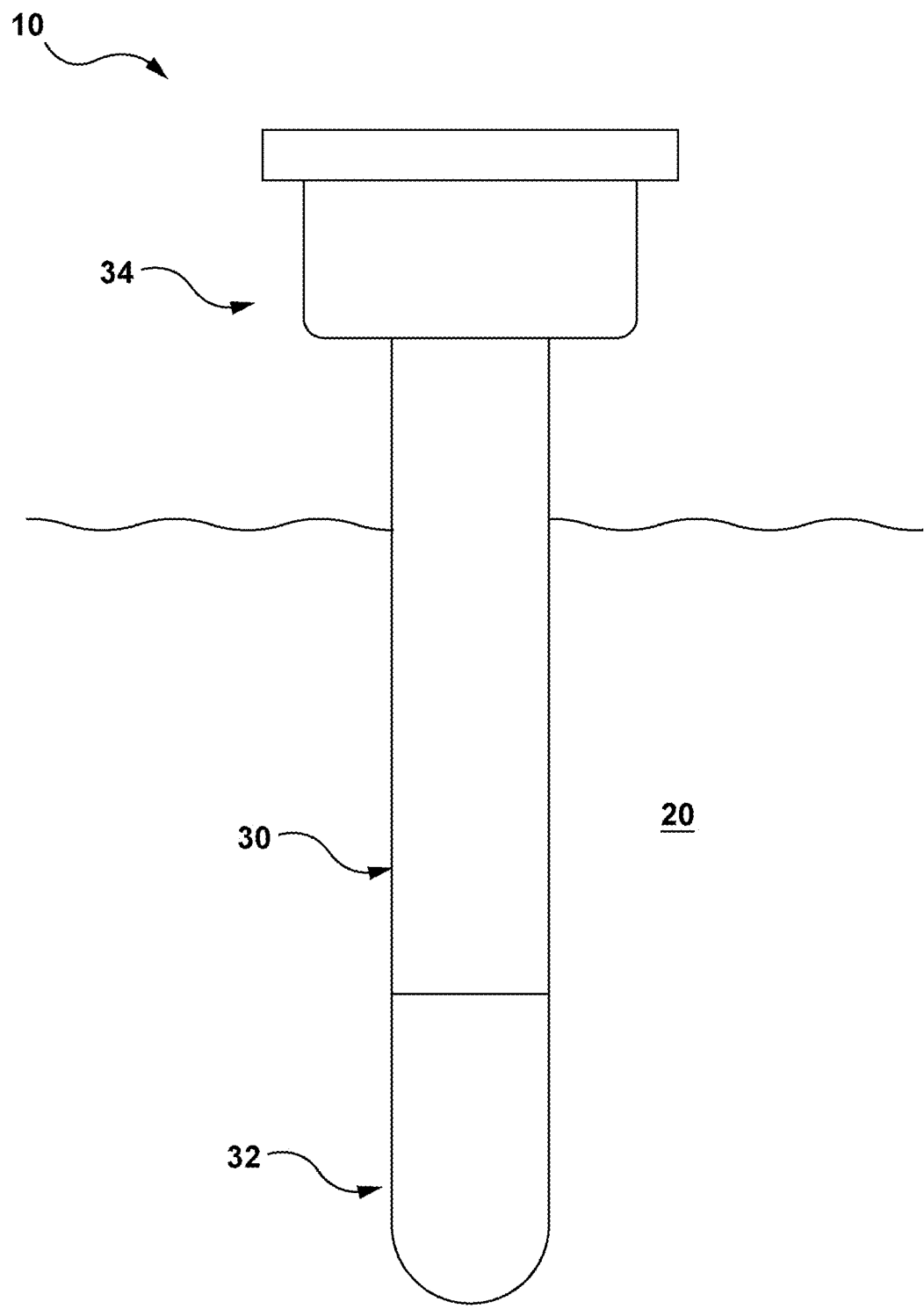
FIG. 1 is a schematic side perspective view of a porous medium parameter measurement device according to one embodiment of the present technology.

Before continuing to describe the present disclosure in further detail, it is to be understood that this disclosure is not limited to specific devices, systems, methods, or uses or process steps, and as such they may vary. It must be noted that, as used in this specification and the appended claims, the singular form "a", "an" and "the" include plural referents unless the context clearly dictates otherwise.

As used herein, the term "about" in the context of a given value or range refers to a value or range that is within 20%, preferably within 10%, and more preferably within 5% of the given value or range.

It is convenient to point out here that "and/or" where used herein is to be taken as specific disclosure of each of the two specified features or components with or without the other. For example, "A and/or B" is to be taken as specific disclosure of each of (i) A, (ii) B and (iii) A and B, just as if each is set out individually herein.

It is to be understood that positional descriptions such as "above", "lower", "upper", "below", "forward", "rearward" "left", "right" and the like should, unless otherwise indicated, be taken in the context of the figures and correspond to the position and orientation of the porous medium parameter measurement devices and corresponding parts when inserted in the porous medium, with the "upper" corresponding to a portion closer to the exposed surface of the porous medium and the "lower" corresponding to a portion opposed to the upper portion.

As used herein, the term "multiplicity" as used in expressions such as "a multiplicity of" relates to the state of being made of multiple diverse elements. As used herein, the term "plurality" as used in expressions such as "a plurality of" relates to the state of being plural.

As used herein, the expression "porous medium" refers to a material containing pores, cavities, channels, voids or a combination thereof. The skeletal portion of the material is referred to herein as the "material body" or "matrix". The pores, cavities, channels or voids are filled with fluids (i.e., liquid, gas) and/or solid components of the porous medium. The porous medium may be characterized by one or more of its porosity, permeability, tensile strength, electrical conductivity, pH, temperature, tortuosity and other physical properties. The porous medium may be of different nature and comprise different components in various proportions. Many natural substances such as rocks and soil (e.g., aquifers, petroleum reservoirs), zeolites, biological tissues (e.g. bones, straw, wood, cork), and manmade materials such as cements and ceramics can be considered as porous media. Further examples of porous media include, but are not limited to, earthen soil or greenhouse soil. The porous medium may be a soil for crop production, which can comprise for instance, sand, peat, bark, coconut fibers, loam, silt, clay, and the like, each in various proportions. The porous medium may also be a porous medium comprising organic and inorganic compounds in various proportions, and be used for instance as a growing medium for greenhouses, nursery production, landscaping and urban agriculture. Soils other than those for crop production are also within the scope of the expression "porous medium". The porous medium can also include a variable content of a water-based solution, for example, a solution eventually leaching out of the porous medium to form the porous medium solution which contains fluids and/or dissolved ionic species and/or other components of the porous medium.

The expression "soil water tension" or "SWT" herein refers to the force necessary for plant roots to extract water from the soil and/or to the degree to which the water clings to the soil.

As used herein, the term "fluid" includes both liquids and gases. As used herein, the term "gas" refers to a fluid (such as, but not limited to, air) that has neither independent shape nor volume but tends to expand indefinitely, whereas the term "liquid", as used herein, refers to a fluid (such as, but not limited to, water) that is nearly incompressible and that conforms to the shape of its container but retains a (nearly) constant volume independent of pressure.

As used herein, the term "tensiometer" refers to a measuring instrument for determining the matric water potential (i.e., soil water tension) in the vadose zone.

Porous medium parameters are influenced by concentration of different ionic species in the porous medium solution which is present in the pores of the porous medium. This porous medium solution needs to be assessed in order to measure various parameters of the porous medium. As such, there is an advantage in increasing the contact area between the porous medium solution and the porous medium measurement device so as to improve the rate and the accuracy of measurement of the porous medium parameters and to allow direct and/or simultaneous measurement of more than one parameter of the porous medium. The PMPM device of the present technology is thus an alternative for the use of several devices to measure several parameters of the porous medium.

The present technology thus stems, in part, from the investigators' findings that alternating layers of porous conductive component and porous non-conductive component in a porous medium measurement (PMPM) device allows the use of these different layers for direct and simultaneous measurement of various parameters of the porous medium solution. In one embodiment, each porous conductive component of the PMPM device of the present technology is in contact with at least one porous non-conductive component thereby increasing the contact area between the porous medium solution and the different conductive layers of the PMPM device.

In particular, the present investigators have found that by modulating and/or adjusting the physical and/or chemical properties of the porous conductive and porous non-conductive components, such by for example, by modifying the shape, the thickness, the porosity, or the like, the overall sensibility and range of measurements of the device may be adjusted or fine-tuned. Direct measurements of various parameters of the porous medium solution are achieved through detection of a change in the state of one or more of the porous conductive components such as, for example, a decrease or increase electromagnetic wave propagation (measured as resistance, impedance, conductance or the like) or by the occurrence of a physical deformation. In some instances, these changes in the state of one or more of the porous conductive components are communicated to a data acquirer or are directly used inside a sequence or mechanism that activates external apparatus to perform an action (such as, but not limited to, opening a valve, starting a pump, filtering, injecting fertilizers or chemical compounds to correct the water quality, or the like). In some instances, these direct measurements allow the PMPM device to operate without a pressure sensor, contrary to conventional tensiometers.

In one embodiment, the present technology relates to a porous medium parameter measurement device comprising at least two components selected from: a porous non-conductive component; a porous conductive component and a selective component. The porous medium parameter measurement device of the present technology allows to directly and simultaneously assess various parameters of the porous medium such as, but not limited to: salinity, water tension, ionic concentration, ionic strength, energy, pH, temperature, or any other parameters that may be assessed or measured from the porous medium solution that is present in the components of the device of the present technology, in particular that is present in the pores of the components of the device of the present technology.

In some embodiments, the porous medium parameter measurement device of the present technology may be used to measure the moisture content in the porous medium.

In some embodiments, the porous medium parameter measurement device of the present technology may be used to measure water tension in the porous medium.

In some embodiments, the porous medium parameter measurement device of the present technology may be used to measure salinity in the porous medium.

In some embodiments, the porous medium parameter measurement device of the present technology may be used to measure electrical conductivity in the porous medium solution.

In some embodiments, the porous medium parameter measurement device of the present technology may be used to simultaneously measure at least moisture content and water tension in the porous medium.

In some embodiments, the porous medium parameter measurement device of the present technology may be used to simultaneously measure at least electrical conductivity of the porous medium solution and water tension and in the porous medium.

In some embodiments, the porous medium parameter measurement device of the present technology may be used to simultaneously measure at least salinity and water tension in the porous medium.

In some embodiments, the porous medium parameter measurement device of the present technology may be used to simultaneously measure at least moisture content, salinity and water tension in the porous medium.

In some embodiments, the porous medium parameter measurement device of the present technology may be used to measure concentration of one or more of the following ions: $NO_3$, $PO_4^{3-}$, $K^+$, $NH_4^+$, $Ca^{2+}$, $Mg^{2+}$, $Na^+$, and Cl in the porous medium. Other elements of the porous medium such as: boron, copper, iron, sulfur, zinc, chromium, lead, cadmium, manganese, mercury, nickel, arsenic, and aluminum may be measured with the porous medium parameter measurement device of the present technology.

In some additional embodiments, the porous medium parameter measurement device of the present technology may be used to measure parameters (e.g., chemical and/or physical properties) of the porous medium such as: its pH, water potential and/or osmotic potential.

In some embodiments, the porous medium parameter measurement device of the present technology may be configured to combine a multiplicity of components (e.g. more than one component of any given type without limitations on the number of components used together) in operative communication with one another and with a porous medium for the simultaneous measurement or assessment of a multiplicity of chemical and/or physical properties of the porous medium and/or porous medium solution such as, for example, the porous medium water tension, the porous medium salinity, the porous medium solution pH, the concentration of the $PO_4^{3-}$ ion and the concentration of the $Mg^{2+}$ ion in the porous medium solution. In other embodiments, the multiplicity of components may allow for the measurement or assessment of different chemical and/or physical properties of the porous medium and/or porous medium solution.

FIG. 1 shows the overall general structure of a porous medium parameter measurement device according to one embodiment of the present technology. In this embodiment, the porous medium parameter measurement (PMPM) device is generally depicted as 10 and is placed vertically into a porous medium 20 (e.g., soil). The PMPM device 10 has an elongated shape to facilitate insertion of the PMPM device 10 into porous medium 20. It will be appreciated that PMPM device 10 may be configured with various other shapes and forms without departing from the present technology. The PMPM device comprises a lower portion 32 which, in use in a vertical position, is inserted in the porous medium 20 and an upper portion 34 which, in use in a vertical position, corresponds to the portion of the PMPM device that is the closest to the surface of the porous medium 20. The PMPM device 10 is airtight sealed or airtight sealable at its upper portion 34. In some instances, the PMPM device 10 may be inserted into the porous medium 20 in a horizontal position (not shown).

Figure 2:
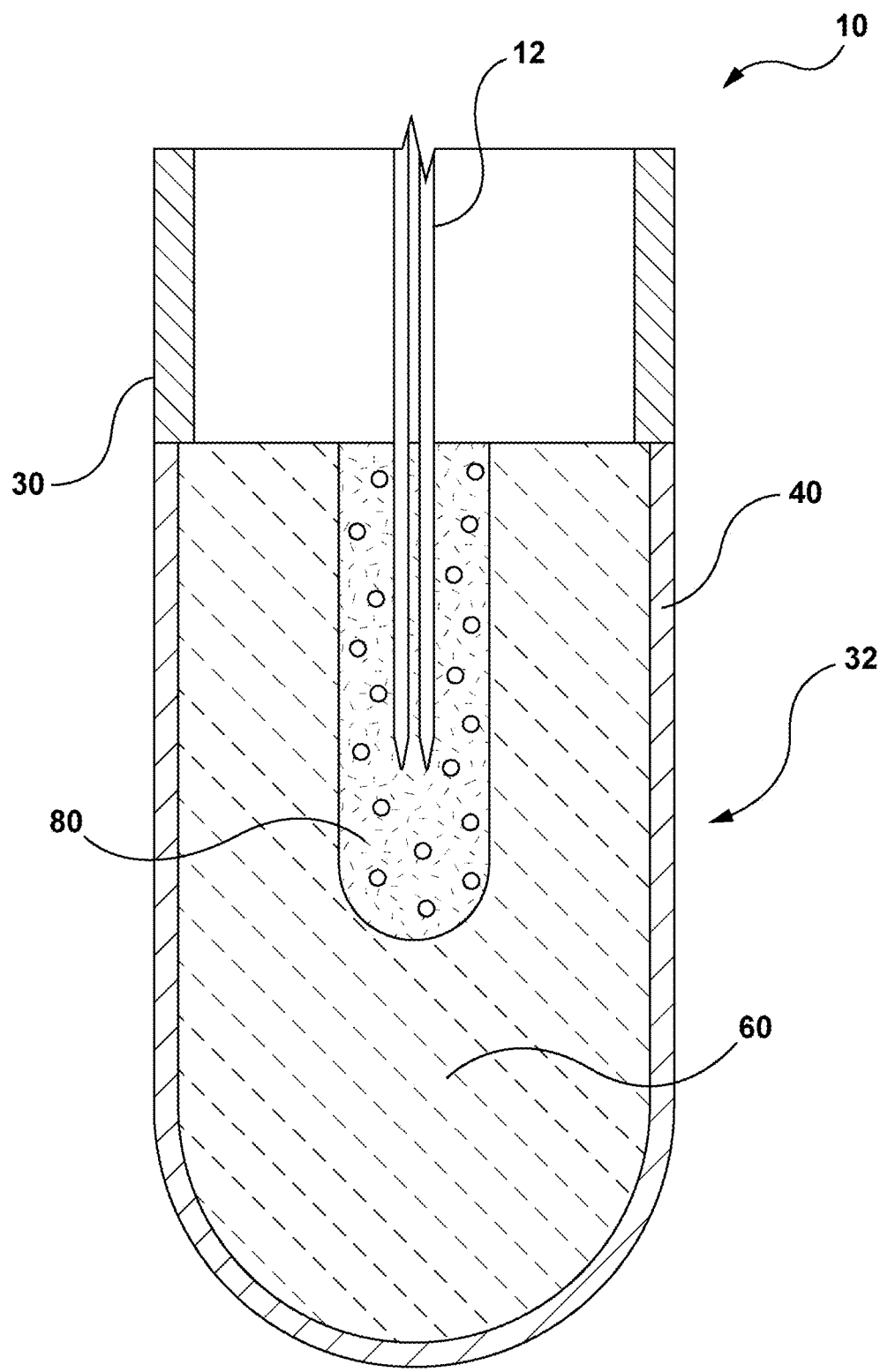
FIG. 2 is a schematic cross-sectional side perspective view of the lower portion of a porous medium parameter measurement device according to another embodiment of the present technology.

FIG. 2 shows the lower portion 32 of the PMPM device 10 in greater details. The lower portion 32 comprises a non-conductive porous component 40, a conductive porous component 60, and a selective component 80. Selective component 80 is made of a conductive porous material, the pores of which are, in some instances, filled with a polymeric substance. A layer of porous conductive component 60 surrounds the selective component 80. The porous conductive component 60 is made of a material having an average pore size that prevents the polymer molecules of the selective component from diffusing through the component or from blocking its pores. Electrodes 12 are immersed in selective component 80. The layer of porous conductive component 60 and the selective component 80 are in operative communication allowing the porous medium solution to diffuse through these components. In this embodiment, a layer of porous non-conductive component 40 surrounds the layer of porous conductive component 60. The layer of porous non-conductive component 40 and the layer of porous conductive component 60 are in operative communication allowing the porous medium solution to diffuse through these components. The layer of porous non-conductive component 40 is in direct contact with the porous medium 20. In some implementations of these embodiments, the porous non-conductive component 40 provides insulation for the porous conductive components and the electrode 12 of the PMPM device 10.

Figure 3:
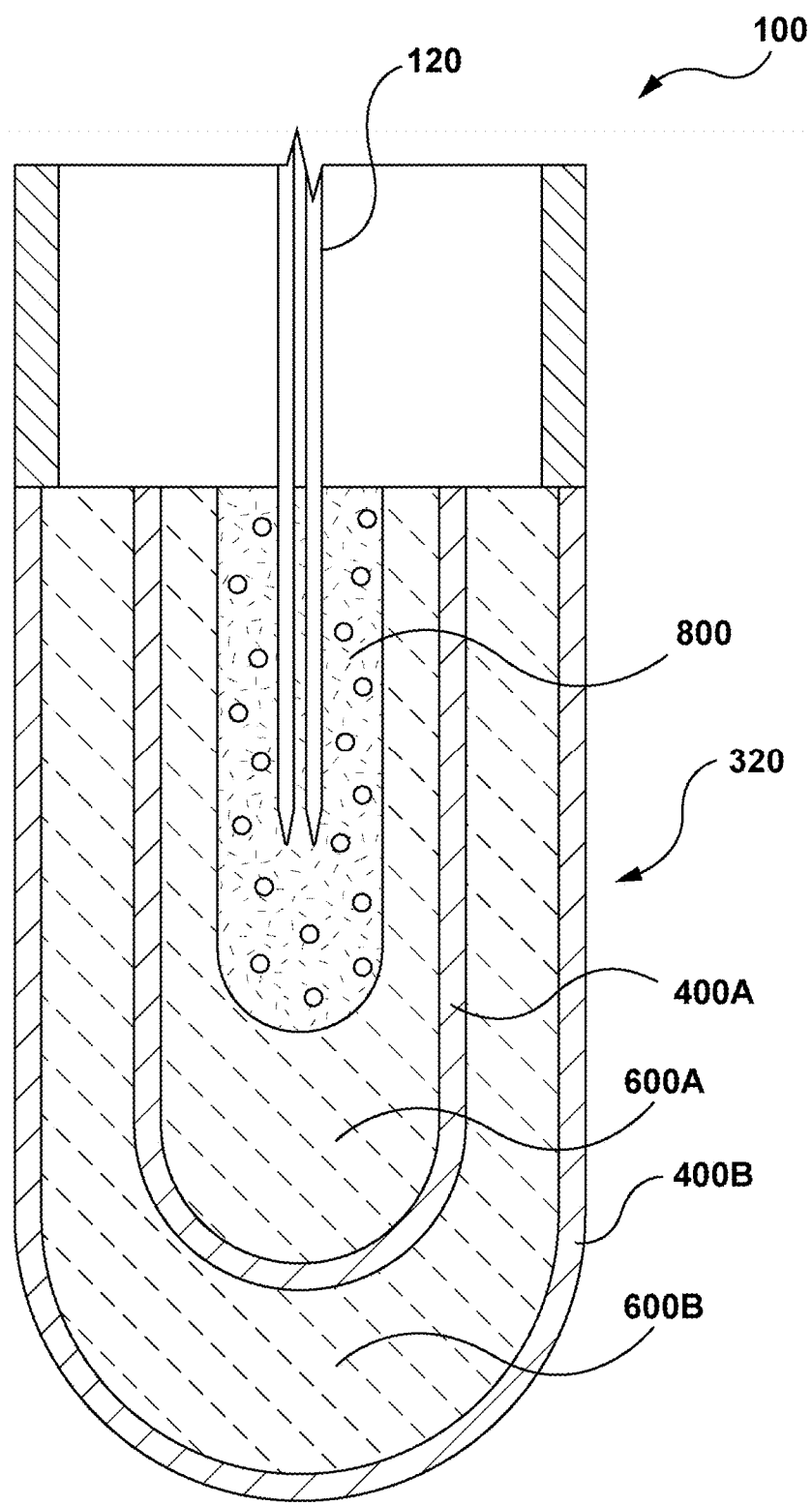
FIG. 3 is a schematic cross-sectional side perspective view of the lower portion of a porous medium parameter measurement device according to a further embodiment of the present technology.

FIG. 3 shows another embodiment of the PMPM device of the present technology. In this embodiment, the PMPM device 100 comprises a lower portion 320 with two layers of porous non-conductive components 400A, 400B, two layers of porous conductive components 600A, 600B, and a selective component 800. Selective component 800 is made of a conductive porous material, the pores of which are filled with a polymeric substance when in use. The first layer of porous conductive component 600A surrounds the selective component 800. The porous conductive component 600A is made of a material having an average pore size that prevents the polymer molecules present in the polymeric substance from diffusing through the component or from blocking the pores. In this embodiment, electrodes 120 are immersed in selective component 800. The first layer of porous conductive component 600A and the selective component 800 are in operative communication allowing the porous medium solution to diffuse through these components. A first layer of porous non-conductive component 400A surrounds the first layer of porous conductive component 600A. The first layer of porous non-conductive component 400A and the first layer of porous conductive component 600A are in operative communication allowing the porous medium solution to diffuse through these components. A second layer of porous conductive component 600B surrounds the first layer of porous non-conductive component 400A and a second layer of porous non-conductive component 400B surrounds the second layer of porous conductive component 600B. The first layer of porous non-conductive component 400A, the second layer of porous conductive component 600B and the second layer of porous non-conductive component 400B are in operative communication allowing the porous medium solution to diffuse through these components. In this embodiment, the second layer of porous non-conductive component 400B is located along the exterior periphery of the lower portion 32 and is in direct contact with the porous medium. In other embodiments, other components may be present on the exterior periphery of the lower portion 32 such as for example a porous housing or casing.

In other embodiments, the PMPM device of the present technology comprises additional layers of non-conductive, conductive and selective components. The number and the configuration of these components will vary depending at least on the measurements that are to be made by the PMPM device.

In some embodiments, the various components of the PMPM device of the present technology may take the form of plaques (e.g., planar or semi-circular, or circular) superposed one on top of the other.

In some embodiments, the PMPM device of the present technology may comprise a single component, the pores of which may be filled with a polymeric substance.

In some instances of these embodiments, the components of the PMPM device (e.g., the conductive components, the non-conductive components and the selective components) are in operative communication such that the porous medium solution diffuses from the exterior of the PMPM device to the electrodes or to any other measuring means present in the PMPM device, such as in each of the different layers of the PMPM device, or between 2 layers. In some implementations, the operative communication is a fluidic communication.

The non-conductive, the conductive and the selective components comprise a plurality of pores suitable to receive the porous medium solution. The plurality of pores increases the overall area of contact between the PMPM device and the porous medium solution, thereby considerably decreasing the response time of the PMPM device. This operative communication represents an advantage of the PMPM device of the present technology over the conventional devices with ceramic cavities by inter alia reducing the distance over which the porous medium solution needs to travel to reach the detectors or other measuring devices (e.g., electrodes). In addition, because the porous medium solution comes to a diffusion equilibrium between the pores of the components and the porous medium, the PMPM device of the present technology allows to measure properties or parameters of the porous medium solution directly (i.e., without the use of empirical equations to derive or convert indirect measurements). In contrast, a conventional salinity probe will measure the electrical conductivity of a soil (e.g., particles, fluids, gas present in the soil) and will use equations to calculate the overall salinity of the soil.

In some other embodiments, the PMPM device of the present technology comprises one or more non-selective component (not shown) or in other embodiments, some of the porous components of the PMPM device could act as non-selective components. In the context of the present technology, a non-selective component could be modified to allow the assessment of other parameters, for example by including an ionophore material into it resulting in the measured electrical conductivity being proportional to the concentration of a specific ion, such as an ion nitrate ($NO_3^-$), in the porous medium solution.

In some implementations, salinity of the porous medium may be determined by measuring conductivity of porous medium solution present in the pores of the conductive component, or another electrical property, such as for example capacitance.

In some implementations, salinity of the porous medium may be determined by measuring conductivity of porous medium solution present in the pores of the non-conductive component, or another electrical property, such as for example capacitance.

In some implementations, ionic concentration, osmotic potential, and/or pH of the porous medium solution may be determined by measuring these properties in the selective component.

In some implementations, ionic concentration, osmotic potential, and/or pH of the porous medium solution may be determined by measuring these properties in the non-selective component.

In some implementations, ionic concentration, osmotic potential, and/or pH of the porous medium solution may be determined by measuring these properties in at least two different components (conductive, non conductive, selective and/or non-selective) of the PMPM device of the present technology.

i) Non-Conductive Component

In some embodiments, the non-conductive component is a porous non-conductive component permeable to the porous medium solution. The non-conductive component comprises a non-conductive porous material. As used herein, the expression "non-conductive" refers to a component or a material that has low or no ability to conduct electrical current. In some instances, the non-conductive porous material has a conductivity value that is between about $1\times10^{-2}$ and about $1\times10^{-4}$ S/m, or between about $1\times10^{-6}$ and about $1\times10^{-8}$ S/m, or between about $1\times10^{-8}$ and about $1\times10^{-20}$ S/m. Examples of a non-conductive porous material that may be used include, but are not limited to: non-conductive ceramic (e.g., hydrophilic ceramic), porous plastic, cork, compressed wood fiber (i.e., fiberboard) or the like). The non-conductive porous material used in the fabrication of the non-conductive component may exhibit an air entry point that is between about 1 kPa and about 100 000 kPa, or between about 100 kPa and about 50 000 kPa, or between about 1000 kPa and about 10 000 kPa, or between about 1 kPa and about 25 000 kPa, or between about 1 kPa and about 10 000 kPa; or about 1100 kPa.

In some instances the non-conductive component has an average thickness of between about 0.1 micron and about 100 microns, between about 100 microns to about 20 mm, between about 100 microns and about 10 mm, between about 100 microns and 5 mm, between about 100 microns and 1 mm, or between about 500 microns and 1 mm, or about 100 microns, about 500 microns, about 1 mm, about 2 mm, about 3 mm, about 4 mm, about 5 mm, about 10 mm, about 15 mm, about 20 mm, or about 50 mm.

In some instances, the non-conductive component comprises a plurality of pores having an average diameter of between about 0.01 micron and about 5 microns, or between about 5 microns to about 50 microns, or between about 5 microns and 35 microns, or between about 10 microns and about 50 microns, or between about 10 microns and about microns.

In some implementations of these embodiments, the non-conductive component has a conical shape. It is to be understood that the non-conductive component may have other shapes without departing from the present technology such as, for example: a toric shape, a cubic shape, a spherical shape, or a disc-like shape.

ii) Conductive Component

In some embodiments, the conductive component is a porous conductive component permeable to fluids from the porous medium. The conductive component comprises a conductive porous material. As used herein, the term "conductive" refers to a component or a material that as the ability to conduct electrical current. In some instances, the conductive porous material has a conductivity value that is between about $1\times10^6$ S/m and about $10\times10^7$ S/m.

Examples of a conductive porous material that may be used include, but are not limited to: conductive ceramic (e.g., hydrophilic ceramic), silver, zirconium, titanium dioxide, steel alloy, graphite, graphene, copper alloy, or the like. The conductive porous material used in the fabrication of the conductive component may exhibit an air entry point that is between about 1 kPa and about 100 000 kPa, or between about 100 kPa and about 50 000 kPa, or between about 1000 kPa and about 10 000 kPa, or between about 1 kPa and about 25 000 kPa, or between about 1 kPa and about 10 000 kPa; or about 1100 kPa.

In some implementations of these embodiments, the conductive component comprises conductive particles. In some instances, the conductive component is enriched or supplemented with conductive particles. The conductive particles are used herein to improve or increase the conductivity of the conductive component. In some instances, the conductive particles are metallic particles. Examples of metallic particles that may be used include but are not limited to: silver particles, aluminum particles, titanium particles, copper particles, zirconium particles or any combination or alloy thereof. In some other instances, the conductive particles are graphite particles.

In some embodiments, the non-conductive component of the present technology is a conductive component that is not enriched or supplemented with conductive particles such that the conductivity of the non-conductive component is lower than the conductivity of the conductive component.

In some instances the conductive component has an average thickness of between about 100 microns to about 20 mm, between about 100 microns and about 10 mm, between about 100 microns and 5 mm, between about 100 microns and 1 mm, or between about 500 microns and 1 mm, or about 100 microns, about 500 microns, about 1 mm, about 2 mm, about 3 mm, about 4 mm, about 5 mm, about 10 mm, about 15 mm or about 20 mm.

In some instances, the conductive component comprises a plurality of pores having an average size of between about 5 microns and about 50 microns, or between about 5 microns and 35 microns, or between about 10 microns and about 50 microns, or between about 10 microns and about 35 microns.

In some implementations of these embodiments, the conductive component has a conical shape. It is to be understood that the conductive component may have other shapes without departing from the present technology such as, for example: a toric shape, a cubic shape, a spherical shape, or a disc-like shape. In some implementations, shape of the conductive component is complementary to the shape of the non-conductive component.

iii) Selective Component

In some embodiments, the selective component is chosen based on the parameters of the porous medium that are to be assessed or measured (e.g., pH, nitrates content, osmotic potential, water potential, temperature, or the like). Depending on the parameters that are to be assessed or measured, the selective component will comprise selective material effective to assess or measure such parameter. In some implementations of these embodiments, the selective component is composed of a conductive material that allows conductive communication with the other components of the PMPM device. In some instances, the selective component is a material that is porous and that can transport ions.

In some implementations of these embodiments, the pores of the conductive material are filled with a polymeric substance. In some instances, the size of the polymers that may be used in the PMPM device of the present technology is between about 0.5 and about 5000 kg/mol.

Examples of polymers that may be used in the device of the present technology include, but not limited to: superabsorbents; hydrogels such as for example: poly (2-hydroxyethyl methacrylate), N-vinylpyrrolidone, copolymer of 2,3-dihydroxypropyl methacrylate, 2-hydroxyethyl methacrylate, polyethylene glycol (PEG) polyvinyl pyrrolidinone gold (PVP), poly (vinyl alcohol) (PVA), poly (N-isopropylacrylamide), poly (acrylamide-co-diallyldimethylammonium chloride), sucrose derivative and cellulose. Further examples of polymers include: non-ionic polyacrylamides.

Other examples of polymeric material that may be used include: polyacrylamide, polyethylene glycol, polyvinyl alcohol, polyvinyl pyrrolidinone, and polyethylenimine. Water-soluble copolymers are also useful as osmotically active species, such as, for example, a copolymer of ethylene glycol with bisphenol A diglycidyl ether. Water-soluble polymers having ionic sites may also be employed as the osmotically active species. Examples of such polymers include sodium carboxymethyl cellulose, poly(diallyl dimethyl ammonium chloride), potassium poly(acrylamido-2-methyl-1-propanesulfonic acid), and sodium polyacrylate. Copolymers such as poly(acrylamide-co-acrylic acid) and their salts may also be employed. Similarly, acid salts of polyethylenimine or other polyamines may be employed as osmotically active polymers having ionic sites.

In some implementations, the selective component of the device of the present technology is a conductive component enriched or supplemented with polymeric material as defined herein.

In some implementations, the selective component of the device of the present technology is a non-conductive component enriched or supplemented with polymeric material as defined herein.

In some embodiments, the selective component is enriched or supplemented with conductive particles as defined herein.

In some embodiments, the selective component is enriched with ionophores.

In some other embodiments, the selective component comprises one or more layer of coating. In some instances, the coating may be a membrane filter. In some other embodiments, the selective component itself may be membrane filter.

In some instances, the selective component comprises a plurality of pores having an average diameter of between about 5 microns to about 50 microns, or between about 5 microns and 35 microns, or between about 10 microns and about 50 microns, or between about 10 microns and about 35 microns.

iv) Additional Components

In some embodiments, the PMPM device of the present technology may comprise one or more additional component. The one more additional component may be additional detection apparatus or measurement apparatus. Additional apparatus that may be used include, but are not limited to, apparatus for optical measurements by absorbance, transmittance, luminescence, spectroscopy, spectroscopy (Raman, SERS), apparatus for electrochemical measurements by standard specific ion electrodes (ISE) or microelectronic adaptations (labchip, chip technologies, etc.), field effect transistor (FET), apparatus for sensitive field effect transistor electrochemical measurements, chemical field effect transistor, electrolyte oxide semiconductor field effect transistor, metal oxide semiconductor field effect transistor, enzymatic field effect transistor, apparatus for chemical or electrochemical reactions on electrodes with suitable surfaces (polymer, nanoparticles, etc.) which may be measured by optics (optodes, optrodes, etc.), apparatus for direct electrical measurements (resistance, conductivity, voltammetry, amperometry, capacitive, potentiometric, etc.), apparatus for microwave measurements.

In some implementations of these embodiments, the additional apparatus may be in direct contact with one or more of the components of the PMPM device such as for example, may be in direct contact with a conductive component and/or with a selective component of the device.

In some embodiments, the porous medium measurement devices of the present technology further comprise a controller. The controller may in the form of a printed circuit board (PCB). The controller may perform various activities such as acquiring, storing, processing, transmitting and/or communicating different soil parameters obtained from sensors of the porous medium measurement device. Examples of different soil parameters that may be processed by the controller include, but are not limited to, the voltage from pressure, temperature, conductance, conductivity, atmospheric pressure, and any other variables. In some instances, the controller may communicate through wiring means (e.g., cable) or wirelessly to a computer at a remote location. In some instances, data obtained by the controller may be transmitted to the computer at fixed interval or only when a variation (e.g., in percentage, or in kPa) occurs. The controller may be powered by a rechargeable energy source placed into the controller or remotely from the controller (e.g., in other parts of the porous medium parameter measurement device). The controller may be equipped with a temperature sensor for measuring temperature of the porous medium.

Although the present porous medium parameter measurement devices of the present technology have been described primarily for measurement of parameters of a porous medium such as a soil, it is to be appreciated that the porous medium parameter measurement devices of the present technology could be applied to measure similar parameters in a reservoir, retention basin, indoor culture, lake, or the like.

INCORPORATION BY REFERENCE

All references cited in this specification, and their references, are incorporated by reference herein in their entirety where appropriate for teachings of additional or alternative details, features, and/or technical background.

EQUIVALENTS

While the disclosure has been particularly shown and described with reference to particular embodiments, it will be appreciated that variations of the above-disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following embodiments.

The invention claimed is:

1. A porous medium parameter measurement device comprising alternating layers of at least one porous conductive component, and at least one porous non-conductive component;
   wherein each one of the alternating layers is in operative communication with a porous medium through a plurality of pores allowing a porous medium solution to diffuse through each one of the alternating layers to reach diffusion equilibrium with the porous medium;
   wherein at least one of the alternating layers is enriched or supplemented with at least one of conducting particles and ionophores; and
   wherein at least two parameters of the porous medium solution are measured, the at least two parameters being different from one another.

2. The porous medium parameter measurement device according to claim 1, wherein the operative communication is a fluid communication.

3. The porous medium parameter measurement device according to claim 1, wherein at least one of the alternating layers is enriched or supplemented with a polymeric material.

4. The porous medium parameter measurement device according to claim 3, wherein the polymeric material comprises a hydrogel.

5. The porous medium parameter measurement device according to claim 1, wherein the at least two parameters of the porous medium solution measured simultaneously are selected from: moisture content, salinity, electric conductivity, water tension, ionic concentration, ionic strength, energy, pH, osmotic potential and temperature.

6. The porous medium parameter measurement device according to claim 1, wherein the conductive particles are metallic particles.

7. The porous medium parameter measurement device according to claim 6, wherein the metallic particles are silver particles, aluminum particles, titanium particles, copper particles, zirconium particles, any combination thereof, or any alloy thereof.

8. The porous medium parameter measurement device according to claim 1, wherein the conductive particles are graphite particles.

9. The porous medium parameter measurement device according to claim 1, wherein the porous non-conductive component comprises hydrophilic non-conductive ceramic.

10. The porous medium parameter measurement device according to claim 1, wherein the porous conductive component comprises hydrophilic conductive ceramic.

11. The porous medium parameter measurement device according to claim 1, wherein the porous conductive component exhibits an air entry point that is between about 1 kPa and about 100 000 kPa.

12. The porous medium parameter measurement device according to claim 1, wherein the porous conductive component exhibits an air entry point that is about 1100 kPa.

13. The porous medium parameter measurement device according to claim 1, wherein pores of the plurality of pores of at least one of the alternating layers have an average size ranging between about 0.01 micron and about 5 microns.

14. The porous medium parameter measurement device according to claim 1, comprising more than one porous conductive component or more than one porous non-conductive component.

* * * * *